United States Patent [19]

Farge et al.

[11] 4,327,095
[45] Apr. 27, 1982

[54] METHOXY DERIVATIVES OF 1,4-DITHIEPINO-[2,3-C]-PYRROLE

[75] Inventors: Daniel Farge, Thiais; Andre Leger, Paris; Gerard Ponsinet, Sucy-En-Brie, all of France

[73] Assignee: Rhone-Poulenc Industries, Paris, France

[21] Appl. No.: 130,132

[22] Filed: Mar. 13, 1980

[30] Foreign Application Priority Data

Mar. 15, 1979 [FR] France ................ 79 06562

[51] Int. Cl.³ ............... A61K 31/385; C07D 513/04
[52] U.S. Cl. .................... 424/250; 544/360;
544/362; 544/363; 544/373; 260/326.5 S
[58] Field of Search .......... 544/373, 362, 363, 360;
260/326.5 S; 424/250

[56]  References Cited
U.S. PATENT DOCUMENTS 3,966,931  6/1976  Jeanmart et al. ............ 544/373
4,016,274  4/1977  Cortel et al. ............... 544/362
4,124,711  11/1978 Jeanmart et al. ............ 544/373

FOREIGN PATENT DOCUMENTS 2341312  2/1976  France ................... 544/373

OTHER PUBLICATIONS

H. R. Schweizer, Helv. Chem. Acta, 52, 2228, (1969).
D. E. Horning, et al., Can. J. Chem. 48, 975–982, (1970).
Tedeshi, et al., J. Pharmacol, 125, 28, (1959).

Swinyard, et al., J. Pharmacol, 106, 319, (1952).
F. Barzachi, et al., Arzneimettel–Forschung, 23, 683, (1973).

Primary Examiner—Donald G. Daus
Assistant Examiner—Sharon A. Gibson
Attorney, Agent, or Firm—Stevens, Davis, Miller & Mosher

[57]  ABSTRACT

Compounds of the formula:

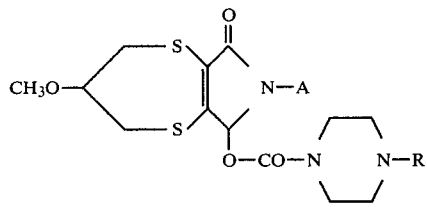

wherein A represents pyrid-2-yl, quinol-2-yl or 1,8-naphthyridin-2-yl, each such radical being optionally substituted by a halogen atom, or an alkyl or alkoxy radical of 1 through 4 carbon atoms, and R represents hydrogen, an alkyl radical of 1 through 4 carbon atoms, an alkenyl radical of 2 through 4 carbon atoms or an alkanoyl radical of 1 through 4 carbon atoms, are new compounds possessing pharmacological properties. They are particularly active as tranquillizers, anti-convulsants, decontracturants and hypnogenic agents.

13 Claims, No Drawings

METHOXY DERIVATIVES OF 1,4-DITHIEPINO-[2,3-C]-PYRROLE

DESCRIPTION

This invention relates to new therapeutically useful 1,4-dithiepino[2,3-c]pyrrole derivatives, processes for their preparation and pharmaceutical compositions containing them.

The new 1,4-dithiepino[2,3-c]pyrrole derivatives of the present invention are those compounds of the general formula:

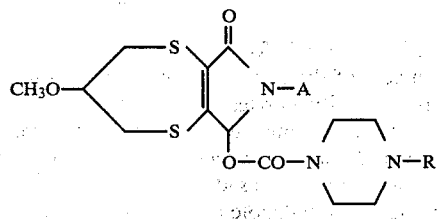

wherein A represents a pyrid-2-yl, quinol-2-yl or 1,8-naphthyridin-2-yl radical, each such radical being optionally substituted by a halogen atom (preferably chlorine), an alkyl radical containing 1 to 4 carbon atoms (preferably methyl) or an alkoxy radical containing 1 to 4 carbon atoms (preferably methoxy), and R represents a hydrogen atom or an alkyl radical containing 1 to 4 carbon atoms (preferably methyl), an alkenyl radical containing 2 to 4 carbon atoms (preferably allyl) or an alkanoyl radical containing 1 to 4 carbon atoms (e.g. propionyl or isobutyryl), and—when appropriate—acid addition salts thereof.

Due to the presence of two asymmetric carbon atoms in the molecule, the compounds of general formula I, and—when appropriate—their acid addition salts, can exist in the form of diastereoisomers; the present invention includes the diastereoisomeric forms of the compounds of general formula I and also mixtures thereof.

According to a feature of the invention, the compounds of general formula I are prepared by the process which comprises reacting a 1-chlorocarbonylpiperazine of the general formula:

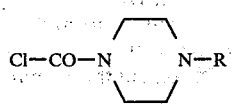

(wherein R is as hereinbefore defined) with a 1,4-dithiepino[2,3-c]pyrrole derivative of the general formula:

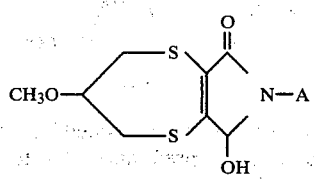

wherein A is as hereinbefore defined.

The reaction can be carried out by reacting a compound of general formula II with a compound of general formula III in the form of an alkali metal salt, optionally prepared in situ, in an anhydrous organic solvent, such as dimethylformamide or tetrahydrofuran, at a temperature below 60° C.

It is also possible to react a compound of general formula II, optionally in the form of an acid addition salt (preferably the hydrochloride), with a compound of general formula III, the reaction being carried out in pyridine and, when an acid addition salt of the reactant of formula II is used, optionally in the presence of a tertiary amine such as triethylamine which liberates the compound of general formula II from its salt.

The 1,4-dithiepino[2,3-c]pyrrole derivatives of general formula III can be obtained by partial reduction of an imide of the general formula:

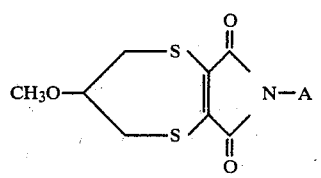

wherein A is as hereinbefore defined. The reduction is generally effected by means of an alkali metal borohydride, in an organic or aqueous-organic solution, for example in a dioxan-tetrahydrofuran or dioxan-methanol or dioxan-water or methanol-water or ethanol-water mixture.

The imides of the general formula IV can be obtained by reacting an amine of the general formula:

$$H_2N—A \qquad V$$

(wherein A is as hereinbefore defined) with the anhydride of 6-methoxy-6,7-dihydro-5H-1,4-dithiepine-2,3-dicarboxylic acid. The reaction is generally carried out by heating the reactants in an organic solvent such as acetic acid, dimethylformamide, acetonitrile or diphenyl ether, or a mixture of such solvents, in the presence or absence of a carbodiimide such as dicyclohexylcarbodiimide or 3-(3-diethylaminopropyl)-1-isopropylcarbodiimide.

The anhydride of 6-methoxy-6,7-dihydro-5H-1,4-dithiepine-2,3-dicarboxylic acid can be prepared by reacting an inorganic base, such as sodium hydroxide, with 3-methoxy-6,8-dioxo-3,4,7,8-tetrahydro-2H,6H-1,4-dithiepino[2,3-c]pyrrole, and then reacting an acid, such as hydrochloric acid, with the resulting mixture.

3-Methoxy-6,8-dioxo-3,4,7,8-tetrahydro-2H,6H-1,4-dithiepino[2,3-c]pyrrole can be obtained by reacting anhydrous hydrogen chloride with a suspension of 6-methoxy-6,7-dihydro-5H-1,4-dithiepine-2,3-dicarbonitrile in formic acid at a temperature below 28° C.

6-Methoxy-6,7-dihydro-5H-1,4-dithiepine-2,3-dicarbonitrile can be obtained by reacting 1,3-dibromo-2-methoxypropane with the disodium salt of 2,3-dimercaptomaleonitrile, the reaction being carried out in an organic solvent, such as dimethylformamide, at a temperature of about 100° C.

1,3-Dibromo-2-methoxypropane can be prepared in accordance with the process described by D. E. Horning et al., Can. J. Chem., 48, 975–982 (1970).

The disodium salt of 2,3-dimercaptomaleonitrile can be prepared in accordance with the process described by H. R. Schweizer, Helv. Chim. Acta., 52, 2228 (1969).

The piperazine derivatives of general formula II, wherein R represents an alkanoyl radical, can be obtained by the action of phosgene in toluene solution at a temperature of about −5° C. on a piperazine derivative of the general formula:

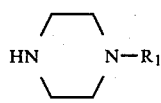

wherein $R_1$ represents the corresponding alkanoyl radical containing 1 to 4 carbon atoms.

The piperazine derivatives of general formula VI can be obtained from piperazine by applying methods known per se for the preparation of amides, such as the action of an acid of the general formula:

$R_2$—COOH                    VII (wherein $R_2$ represents a hydrogen atom or an alkyl radical containing 1 to 3 carbon atoms), or of a derivative of such an acid such as a halide, an ester, the anhydride, a mixed anhydride, the amide or the azide, on piperazine. The piperazine derivatives of general formula VI can be separated from the disubstituted piperazine, which is formed simultaneously, by application of physical or chemical methods.

According to another feature of the invention, the compounds of general formula I are prepared by the process which comprises reacting a piperazine of the general formula:

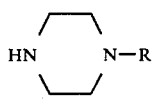

(wherein R is as hereinbefore defined) with a mixed carbonate of the general formula:

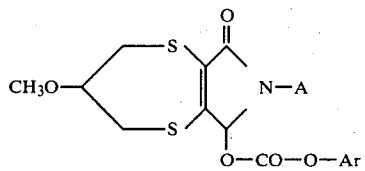

wherein A is as hereinbefore defined and Ar represents a phenyl radical which is optionally substituted by an alkyl radical containing 1 to 4 carbon atoms or by a nitro radical. The reaction is generally carried out in an anhydrous organic solvent such as acetonitrile at a temperature between 0° and 50° C.

The mixed carbonates of general formula IX can be obtained by reacting a chloroformate of the general formula:

Cl—CO—O—Ar                    X (wherein Ar is as hereinbefore defined) with a 1,4-dithiepino[2,3-c]pyrrole derivative of general formula III. The reaction is generally carried out in a basic organic solvent such as pyridine or in an organic solvent such as tetrahydrofuran in the presence of an alkaline condensation agent.

According to a still further feature of the invention, the compounds of general formula I, wherein R represents an alkanoyl radical, are prepared by reacting an acid of general formula VII, or a reactive derivative of the acid such as a halide (preferably the chloride), the anhydride, a mixed anhydride, the amide or the azide, with a compound of general formula I wherein R represents a hydrogen atom, that is to say a compound of the general formula:

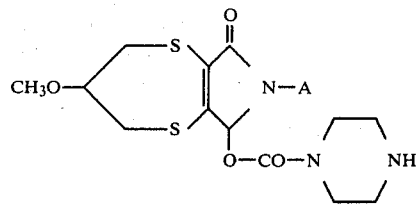

wherein A is as hereinbefore defined.

When an acid of the general formula VII is used, the reaction is generally carried out in an inert organic solvent, such as acetonitrile, methylene chloride, dimethylformamide or ethyl acetate, in the presence of a condensation agent such as dicyclohexylcarbodiimide or N,N-carbonyl-diimidazole at a temperature between 20° and 60° C.

When a halide of an acid of general formula VII (preferably the chloride) is used, the reaction is carried out in an organic solvent such as methylene chloride in the presence of an acid acceptor, for example pyridine or triethylamine, at a temperature between 0° and 30° C.

When the anhydride of an acid of general formula VII or a mixed anhydride is used, the reaction is generally carried out by heating the reactants at a temperature of between 30° and 100° C.

When the amide of an acid of general formula VII is used, the reaction is generally carried out by heating at a temperature above 100° C., optionally in an organic solvent such as an aromatic hydrocarbon and preferably in the presence of iodine.

When the azide of an acid of general formula VII is used, the reaction is generally carried out in an organic solvent such as dioxan in the presence of magnesium oxide at a temperature between 25° and 60° C.

The compounds of general formula XI can be obtained by the action of 1-chlorocarbonylpiperazine on a 1,4-dithiepino[2,3-c]pyrrole derivative of general formula III or by the action of piperazine on a mixed carbonate of general formula IX.

The compounds of general formula XI can also be obtained, according to another feature of the invention, from a compound of the general formula:

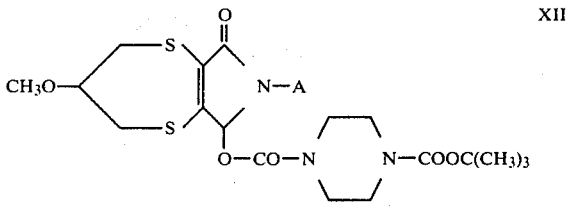

(wherein A is as hereinbefore defined) by treatment with trifluoroacetic acid, preferably at a temperature between 0° and −10° C.

The compounds of general formula XII can be obtained by the action of 4-chlorocarbonyl-1-t.-butoxycarbonylpiperazine on a 1,4-dithiepino[2,3-c]-pyrrole derivative of general formula III. The reaction is generally carried out in an organic solvent such as methylene chloride in the presence of an acid acceptor, for example pyridine or triethylamine, at a temperature between 0° and 30° C.

4-Chlorocarbonyl-1-t.-butoxycarbonylpiperazine can be obtained by the action of phosgene, in toluene solution, on 1-t.-butoxycarbonylpiperazine at a temperature of about −5° C.

1-t.-Butoxycarbonylpiperazine can be obtained by the action of piperazine hydrochloride on t.-butyl azidoformate.

The diastereoisomeric forms of the products of general formula I can be separated from their mixtures by applying physico-chemical methods such as fractional crystallisation.

The 1,4-dithiepino[2,3-c]pyrrole derivatives of general formula I obtained by the aforementioned processes can be purified by physical methods such as crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The compounds of general formula I, and more particularly those wherein R represents a hydrogen atom or an alkyl or alkenyl radical, may be converted by methods known per se into acid addition salts.

The acid addition salts may be obtained by the action of acids on the new compounds in appropriate solvents. As organic solvents there may be used alcohols, ketones, ethers or chlorinated hydrocarbons. The salt which is formed is precipitated, if necessary after concentration of the solution, and is isolated by filtration or decantation.

In French Pat. No. 2,341,312 and U.S. Pat. No. 4,124,711 there are disclosed 1,4-dithiepino[2,3-c]pyrrole derivatives which are active as tranquillisers, anticonvulsants, decontracturants and hypnogenic agents.

It has been found that the compounds according to the present invention, the structure of which differs from that of the compounds of the prior art by the presence of a methoxy group on the dithiepino[2,3-c]-pyrrole ring, exhibit a greater activity than their non-methoxylated homologues.

The compounds of general formula I and, where appropriate, their acid addition salts therefore possess valuable pharmacological properties. They are particularly active as tranquillisers, anti-convulsants, decontracturants and hypnogenic agents.

In animals (mice), they have proved active as such at doses of between 0.5 and 25 mg/kg animal body weight administered orally, in particular in the following tests:

(i) the electrical battle test according to a technique similar to that of Tedeshi et al., J. Pharmacol., 125, 28 (1959), (ii) the pentetrazole-induced convulsion test according to a technique similar to that of Everett and Richards, J. Pharmacol., 81, 402 (1944), (iii) the supramaximal electroshock testing according to the technique of Swinyard et al., J. Pharmacol., 106, 319 (1952), (iv) the strychnine mortality test according to a technique similar to that of F. Barzaghi et al., Arzneimittel-Forschung, 23, 683 (1973), and (v) the locomotor activity test according to the technique of Courvoisier, Congrès des Médecins Alienistes et Neurologistes, Tours, 8th–13th June 1959, and Julou, Bulletin de la Société de Pharmacie de Lille, No. 2, January 1967, page 7.

Furthermore, these compounds exhibit the advantage of having a long duration of action.

The compounds of general formula I exhibit a low toxicity; their $LD_{50}$ when administered orally to mice is generally greater than 900 mg/kg animal body weight.

Preferred 1,4-dithiepino[2,3-c]pyrrole derivatives of the invention are those of general formula I wherein A represents a pyrid-2-yl or 1,8-naphthyridin-2-yl radical optionally substituted by a halogen (preferably chlorine) atom or an by an alkoxy radical containing 1 to 4 carbon atoms (preferably methoxy), and R represents an alkyl radical containing 1 to 4 carbon atoms (preferably methyl), and in particular 7-(7-chloro-1,8-naphthyridin-2-yl)-3-methoxy-6-(4-methylpiperazin-1-yl)carbonyloxy-8-oxo-3,4,7,8-tetrahydro-2$\underline{H}$,6$\underline{H}$-1,4-dithiepino[2,3-c]pyrrole.

For therapeutic purposes, the 1,4-dithiepino[2,3-c]pyrrole derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, theophylline-acetates, salicylates, phenolphthalinates and methylene-bis-β-hydroxynaphthoates) so that the beneficial physiological properties inherent in the bases are not vitiated by side effects ascribable to the anions.

The following non-limitative Examples illustrate the invention.

EXAMPLE 1

Triethylamine (42 cc) is added, at about 15° C., to a suspension of 7-(5-chloropyrid-2-yl)-6-hydroxy-3-methoxy-8-oxo-3,4,7,8-tetrahydro-2$\underline{H}$,6$\underline{H}$-1,4-dithiepino[2,3-c]pyrrole (7.4 g) and 1-chlorocarbonyl-4-methylpiperazine hydrochloride (43.0 g) in anhydrous methylene chloride (215 cc), and anhydrous pyridine (90 cc) is then added to the resulting mixture. The reaction mixture is heated for 10 hours at 45° C. After cooling, the mixture is diluted by adding methylene chloride (250 cc). The organic phase is washed three times with an N aqueous sodium hydroxide solution (total 300 cc) and three times with distilled water (total 750 cc), dried over anhydrous sodium sulphate and evaporated. The residue is dissolved in boiling ethanol (50 cc). After cooling the solution for 20 hours at 2° C., the resulting crystals are filtered off, washed three times with ice-cooled ethanol (total 30 cc) and dried under reduced pressure (20 mm Hg). The resulting product (5.1 g; m.p. 197° C.) is dissolved in boiling ethanol (80 cc). After filtering the boiling solution and then cooling the filtrate for 16 hours at 2° C., the resulting crystals are filtered off, washed with ice-cooled ethanol (8 cc) and dried under reduced pressure (0.2 mm Hg) at 55° C. 7-(5-Chloropyrid-2-yl)-3-methoxy-6-(4-methylpiperazin-1-yl)carbonyloxy-8-oxo-3,4,7,8-tetrahydro-2$\underline{H}$,6$\underline{H}$-1,4-dithiepino[2,3-c]-pyrrole (3.2 g), which melts at 199° C., is obtained.

7-(5-Chloropyrid-2-yl)-6-hydroxy-3-methoxy-8-oxo-3,4,7,8-tetrahydro-2$\underline{H}$,6$\underline{H}$-1,4-dithiepino-[2,3-c]pyrrole used as starting material can be prepared in the following manner:

Preparation of the disodium salt of 2,3-dimercaptomaleonitrile in accordance with the method of H. R. Schweizer, Helv. Chim. Acta, 52, 2228 (1969).

Preparation of 1,3-dibromo-2-methoxypropane (b.p. 98° C./28 mm Hg) in accordance with the method of D. E. Horning et al., Can. J. Chem., 48, 975–982 (1970).

Preparation of 6-methoxy-6,7-dihydro-5H-1,4-dithiepine-2,3-dicarbonitrile (m.p. 105° C.; 44.4 g) by reacting 1,3-dibromo-2-methoxypropane (116 g) with the disodium salt of 2,3-dimercaptomaleonitrile (155 g) in dimethylformamide (1.25 liters) at about 95°–100° C.

Preparation of 3-methoxy-6,8-dioxo-3,4,7,8-tetrahydro-2H,6H-1,4-dithiepino[2,3-c]pyrrole (m.p. 185° C.; 237 g) by reacting anhydrous hydrogen chloride with a suspension of 6-methoxy-6,7-dihydro-5H-1,4-dithiepine-2,3-dicarbonitrile (217 g) in formic acid (2600 cc) at a maximum of 28° C.

Preparation of the anhydride of 6-methoxy-6,7-dihydro-5H-1,4-dithiepine-2,3-dicarboxylic acid (m.p. 141° C.; 162.3 g) by reacting a 5.4 N aqueous solution of sodium hydroxide (222 cc) in distilled water (1100 cc), under reflux, for 30 minutes, with 3-methoxy-6,8-dioxo-3,4,7,8-tetrahydro-2H,6H-1,4-dithiepino[2,3-c]pyrrole (237 g) and then reacting an 11.8 N aqueous solution of hydrochloric acid (150 cc) with the resulting mixture.

Preparation of 7-(5-chloropyrid-2-yl)-3-methoxy-6,8-dioxo-3,4,7,8-tetrahydro-2H,6H-1,4-dithiepino[2,3-c]pyrrole (m.p. 217° C.; 13.5 g) by reacting 2-amino-5-chloropyridine (6.4 g) with the anhydride of 6-methoxy-6,7-dihydro-5H-1,4-dithiepine-2,3-dicarboxylic acid (11.6 g) in diphenyl ether (25 cc) at 170°–180° C. for 1 hour, in the presence of acetic acid (0.4 cc).

Preparation of 7-(5-chloropyrid-2-yl)-6-hydroxy-3-methoxy-8-oxo-3,4,7,8-tetrahydro-2H,6H-1,4-dithiepino[2,3-c]pyrrole (m.p. 147° C.; 7.5 g) by reacting potassium borohydride (1.8 g) with 7-(5-chloropyrid-2-yl)-3-methoxy-6,8-dioxo-3,4,7,8-tetrahydro-2H,6H-1,4-dithiepino[2,3-c]pyrrole (13.5 g) in a mixture of tetrahydrofuran (120 cc) and methanol (36 cc) at a temperature between −10° C. and +20° C.

EXAMPLE 2

Triethylamine (29.5 cc) is added, at about 15° C., to a suspension of 7-(7-chloroquinol-2-yl)-6-hydroxy-3-methoxy-8-oxo-3,4,7,8-tetrahydro-2H,6H-1,4-dithiepino[2,3-c]pyrrole (6.0 g) and 1-chlorocarbonyl-4-methylpiperazine hydrochloride (30.2 g) in anhydrous methylene chloride (150 cc), and anhydrous pyridine (65 cc) is then added to the resulting mixture. The reaction mixture is heated for 10 hours at 45° C. After cooling, the mixture is diluted by adding methylene chloride (300 cc). The organic phase is washed twice with an N aqueous sodium hydroxide solution (total 600 cc) and five times with distilled water (total 1000 cc), dried over sodium sulphate and evaporated. The residue is treated with boiling ethanol (50 cc). After cooling the mixture for 1 hour at 2° C., the crystals are filtered off, washed twice with ice-cooled ethanol (total 20 cc) and dried under reduced pressure (20 mm Hg). The resulting product (4.6 g; m.p. 228° C.) is dissolved in a boiling mixture of acetonitrile (50 cc) and ethanol (150 cc). After cooling the solution for 16 hours at 2° C., the resulting crystals are filtered off, washed with ice-cooled ethanol (5 cc) and dried under reduced pressure (0.2 mm Hg) at 55° C. 7-(7-Chloroquinol-2-yl)-3-methoxy-6-(4-methylpiperazin-1-yl)carbonyloxy-8-oxo-3,4,7,8-tetrahydro-2H,6H-1,4-dithiepino[2,3-c]pyrrole (3.3 g), melting at 228° C., is obtained.

7-(7-Chloroquinol-2-yl)-6-hydroxy-3-methoxy-8-oxo-3,4,7,8-tetrahydro-2H,6H-1,4-dithiepino[2,3-c]pyrrole used as starting material can be prepared in the following manner:

Preparation of 7-(7-chloroquinol-2-yl)-3-methoxy-6,8-dioxo-3,4,7,8-tetrahydro-2H,6H-1,4-dithiepino[2,3-c]pyrrole (m.p. 170° C.; 6.1 g) by reacting 2-amino-7-chloroquinoline (3.6 g) with the anhydride of 6-methoxy-6,7-dihydro-5H-1,4-dithiepine-2,3-dicarboxylic acid (4.65 g) in diphenyl ether (10 cc) at 170°–180° C. for ½ hour in the presence of acetic acid (0.1 cc).

Preparation of 7-(7-chloroquinol-2-yl)-6-hydroxy-3-methoxy-8-oxo-3,4,7,8-tetrahydro-2H,6H-1,4dithiepino[2,3-c]pyrrole (6.0 g) by reacting sodium borohydride (0.46 g) with 7-(7-chloroquinol-2-yl)-3-methoxy-6,8-dioxo-3,4,7,8-tetrahydro-2H,6H-1,4-dithiepino[2,3-c]pyrrole (6.0 g) in a mixture of tetrahydrofuran (52 cc) and methanol (20 cc) at between −12° C. and +2° C.

EXAMPLE 3

Triethylamine (144 cc) is added, at about 15° C., to a suspension of 7-(7-chloro-1,8-naphthyridin-2-yl)-6-hydroxy-3-methoxy-8-oxo-3,4,7,8-tetrahydro-2H,6H-1,4-dithiepino[2,3-c]pyrrole (36.0 g) and 1-chlorocarbonyl-4-methylpiperazine hydrochloride (162 g) in anhydrous methylene chloride (900 cc), and anhydrous pyridine (360 cc) is then added to the resulting mixture. The reaction mixture is heated for 5 hours at 45° C. After cooling, the mixture is diluted by adding methylene chloride (900 cc). The organic phase is washed three times with distilled water (total 750 cc), dried over anhydrous sodium sulphate and evaporated. The residue is treated with boiling ethanol (750 cc). After cooling the mixture for 2 hours at 2° C., the crystals are filtered off, washed with ice-cooled ethanol (100 cc) and then twice with distilled water (total 200 cc) and dried in air. The resulting product (36.5 g; m.p. 206° C.) is dissolved in boiling acetonitrile (3000 cc). After cooling the solution for 3 hours at 20° C., the resulting crystals are filtered off, washed twice with acetonitrile (total 200 cc) and dried under reduced pressure (0.2 mm Hg) at 50° C. 7-(7-Chloro-1,8-naphthyridin-2-yl)-3-methoxy-6-(4-methylpiperazin-1-yl)-carbonyloxy-8-oxo-3,4,7,8-tetrahydro-2H,6H-1,4-dithiepino[2,3-c]pyrrole (26.6 g), melting at 250° C., is obtained (in the form of a mixture of virtually equal amounts of the A and B forms of the diastereoisomers).

7-(7-Chloro-1,8-naphthyridin-2-yl)-6-hydroxy-3-methoxy-8-oxo-3,4,7,8-tetrahydro-2H,6H-1,4-dithiepino[2,3-c]pyrrole used as starting material can be prepared in the following manner:

Preparation of 7-(7-chloro-1,8-naphthyridin-2-yl)-3-methoxy-6,8-dioxo-3,4,7,8-tetrahydro-2H,6H-1,4-dithiepino[2,3-c]pyrrole (m.p. 264° C.; 72.6 g) by reacting 2-amino-7-chloro-1,8-naphthyridine (48.3 g) and 3-(3-diethylaminopropyl)-1-isopropylcarbodiimide (53.0 g) with the anhydride of 6-methoxy-6,7-dihydro-5H-1,4-dithiepine-2,3-dicarboxylic acid (62.4 g) in acetonitrile (625 cc) at 55°–60° C. for 8 hours.

Preparation of 7-(7-chloro-1,8-naphthyridin-2-yl)-6-hydroxy-3-methoxy-8-oxo-3,4,7,8-tetrahydro-2H,6H-1,4-dithiepino[2,3-c]pyrrole (m.p. 150° C.; 130.8 g) by reacting a solution of potassium borohydride (19.7 g) in distilled water (450 cc) with 7-(7-chloro-1,8-naphthyridin-2-yl)-3-methoxy-6,8-dioxo-3,4,7,8-tetrahydro-2H,6H-1,4-dithiepino[2,3-c]pyrrole (143 g) in methanol (1800 cc) at between 30° and 35° C. or 1½ hours.

The mixture of the A and B forms of the diasteroisomers can be separated in the following manner:

Preparation of 1:1 mixture (36.6 g) in accordance with the procedure described above (the proportion of the diastereoisomers is determined by high performance thin layer chromatographic analysis).

Obtention of the A form

Fractional crystallisations are carried out by following the procedure shown in the following Table.

TABLE

| No. of recrystal- lisation | Solvent used | | Recrystal- lisation time | Washing solvent | Weight obtained | Composition % | |
|---|---|---|---|---|---|---|---|
| | | | | | | A form | B form |
| 1 | Acetonitrile: DMF: | 1360 cc 340 cc | 3 hours at 20° C. 1 hour at 20° C. | Acetonitrile: 40 cc | 23.0 g | 70 | 30 |
| 2 | Acetonitrile: | 2400 cc | 3 hours at 2° C. | Acetonitrile: 40 cc | 15.4 g | 80 | 20 |
| 3 | Acetonitrile: DMF: | 1620 cc 180 cc | 1 hour at 20° C. 3 hours at 2° C. | Acetonitrile: 60 cc | 10.6 g | 87 | 13 |
| 4 | Acetonitrile: DMF: | 1080 cc 120 cc | 1 hour at 20° C. 3 hours at 2° C. | Acetonitrile: 60 cc | 8.6 g | 92 | 8 |
| 5 | Acetonitrile: DMF: | 900 cc 100 cc | 1 hour at 20° C. 3 hours at 2° C. | Acetonitrile: 50 cc | 6.8 g | 96 | 4 |
| 6 | Acetonitrile: DMF: | 828 cc 92 cc | 1 hour at 20° C. 3 hours at 2° C | Acetonitrile: 50 cc | 5.6 g | >97 | <3 |

DMF = dimethylformamide

After drying at 80° C. under reduced pressure (0.2 mm Hg), the A form of 7-(7-chloro-1,8-naphthyridin-2-yl)-3-methoxy-6-(4-methylpiperazin-1-yl)-carbonyloxy-8-oxo-3,4,7,8-tetrahydro-2H,6H-1,4-dithiepino[2,3-c]pyrrole (5.6 g), which contains less than 3% of the B form and melts at 288° C., is obtained.

The mother liquors from recrystallisation No. 1 are evaporated to dryness under reduced pressure (20 mm Hg and then 0.2 mm Hg) at a temperature below 50° C. The resulting crystals (13.6 g) are recrystallised six times from acetonitrile, as indicated in the Table for the preparation of the B form; the recrystallisation times are identical for each of the recrystallisations (1 hour at 20° C. and then 3 hours at 2° C.).

The mother liquors from recrystallisation No. 2 for the obtention of the A form are evaporated to dryness under reduced pressure (20 mm Hg and then 0.2 mm Hg) at a temperature below 50° C. The resulting crystals (7.0 g) are recycled to recrystallisation No. 5 for the obtention of the B form.

| No. of recrystal- lisation | Preparation of the B form | | | | |
|---|---|---|---|---|---|
| | Amount of aceto- nitrile | Aceto- nitrile for washing | Weight obtained | Composition % | |
| | | | | A form | B form |
| 1 | 1300 cc | 30 cc | 11.0 g | 30 | 70 |
| 2 | 900 cc | 20 cc | 8.1 g | <30 | >70 |
| 3 | 650 cc | 20 cc | 6.2 g | 25 | 75 |
| 4 | 550 cc | 20 cc | 4.8 g | 20 | 80 |
| 5 | 1300 cc | 40 cc | 5.55 g | <10 | >90 |
| 6 | 600 cc | 20 cc | 4.2 | <2 | >98 |

After drying at 60° C. under reduced pressure (0.2 mm Hg), the B form of 7-(7-chloro-1,8-naphthyridin-2-yl)-3-methoxy-6-(4-methylpiperazin-1-yl)carbonyloxy-8-oxo-3,4,7,8-tetrahydro-2H,6H-1,4-dithiepino[2,3-c]-pyrrole (4.2 g), which contains less than 2% of the A form and melts at 255° C., is obtained.

EXAMPLE 4

The procedure of Example 3 is followed except that 7-(7-chloro-1,8-naphthyridin-2-yl)-6-hydroxy-3-methoxy-8-oxo-3,4,7,8-tetrahydro-2H,6H-1,4-dithiepino[2,3-c]pyrrole (7.9 g) and 4-allyl-1-chlorocarbonylpiperazine hydrochloride (13.5 g) in a mixture of methylene chloride (200 cc) and anhydrous pyridine (80 cc), in the presence of triethylamine (32 cc) are heated at 45° C. for 3 hours. After recrystallisation of the product from dimethylformamide (120 cc), 6-(4-allylpiperazin-1-yl)-carbonyloxy-7-(7-chloro-1,8-naphthyridin-2-yl)-3-methoxy-8-oxo-3,4,7,8-tetrahydro-2H,6H-1,4-dithiepino[2,3-c]pyrrole (7.5 g), melting at 255° C., is obtained.

4-Allyl-1-chlorocarbonylpiperazine hydrochloride can be prepared from 1-allylpiperazine (63.0 g) and phosgene (99.0 g) in diethyl ether (400 cc) at 0° C. 4-Allyl-1-chlorocarbonylpiperazine hydrochloride (86.1 g), which decomposes at about 200° C., is thus obtained.

EXAMPLE 5

The procedure of Example 3 is followed except that 7-(7-chloro-1,8-naphthyridin-2-yl)-6-hydroxy-3-methoxy-8-oxo-3,4,7,8-tetrahydro-2H,6H-1,4-dithiepino[2,3-c]pyrrole (7.9 g) and 1-chlorocarbonyl-4-propionylpiperazine (8.2 g) in a mixture of methylene chloride (100 cc) and anhydrous pyridine (40 cc), in the presence of triethylamine (2.8 cc), are heated at 45° C. for 2 hours. After recrystallisation of the product from acetonitrile (140 cc), 7-(7-chloro-1,8-naphthyridin-2-yl)-3-methoxy-8-oxo-6-(4-propionylpiperazin-1-yl)-carbonyloxy-3,4,7,8-tetrahydro-2H,6H-1,4-dithiepino[2,3-c]pyrrole (6.5 g), melting at 216° C., is obtained.

1-Chlorocarbonyl-4-propionylpiperazine can be prepared in the following manner:

Preparation of 1-propionylpiperazine (b.p 110° C./1 mm Hg; hydrochloride: m.p. 167° C.) (1020 g) by reacting anhydrous piperazine (1135 g) with propionamide (965 g) in anhydrous xylene (965 cc), under reflux, for 48 hours, in the presence of resublimed iodine (8 g).

Preparation of 1-chloroformyl-4-propionylpiperazine (oil, 552 g) by reacting phosgene (297 g) with 1-propionylpiperazine (852 g) in anhydrous toluene (12 liters), at 0° C.

EXAMPLE 6

Triethylamine (34.5 cc) is added, at about 15° C., to a suspension of 6-hydroxy-3-methoxy-7-(7-methoxy-1,8-naphthyridin-2-yl)-8-oxo-3,4,7,8-tetrahydro-2$\underline{H}$,6$\underline{H}$-1,4-dithiepino[2,3-c]pyrrole (10.7 g) and 1-chlorocarbonyl-4-methylpiperazine hydrochloride (16.4 g) in anhydrous methylene chloride (440 cc), and anhydrous pyridine (195 cc) is then added to the resulting mixture. The reaction mixture is heated for 3 hours at 45° C. After cooling, the mixture is diluted by adding methylene chloride (300 cc). The organic phase is washed three times with distilled water (total 600 cc), dried over anhydrous sodium sulphate and evaporated. The resulting residue (41.0 g) is treated with boiling methanol (150 cc). After cooling the mixture for 1 hour at 2° C., the crystals are filtered off, washed twice with ice-cooled methanol (total 40 cc) and dried under reduced pressure (20 mm Hg) at 20° C. The resulting product (9.0 g; m.p. 215° C.) is dissolved in boiling methanol (175 cc). After cooling the solution for 2 hours at 2° C., the resulting crystals are filtered off, washed twice with ice-cooled methanol (total 20 cc) and dried under reduced pressure (0.2 mm Hg) at 50° C. 3-Methoxy-7-(7-methoxy-1,8-naphthyridin-2-yl)-6-(4-methylpiperazin-1-yl)carbonyloxy-8-oxo-3,4,7,8-tetrahydro-2$\underline{H}$,6$\underline{H}$-1,4-dithiepino[2,3-c]pyrrole (7.4 g), melting at 218° C., is obtained.

6-Hydroxy-3-methoxy-7-(7-methoxy-1,8-naphthyridin-2-yl)-8-oxo-3,4,7,8-tetrahydro-2$\underline{H}$,6$\underline{H}$-1,4-dithiepino[2,3-c]pyrrole used as starting material can be prepared in the following manner:

Preparation of 6,8-dioxo-3-methoxy-7-(7-methoxy-1,8-naphthyridin-2-yl)-3,4,7,8-tetrahydro-2$\underline{H}$,6H-1,4-dithiepino[2,3-c]pyrrole (m.p. 196° C.; 11.6 g) by reacting 2-amino-7-methoxy-1,8-naphthyridine (7.5 g) and 3-(3-diethylaminopropyl)-1-isopropylcarbodiimide (8.5 g) with the anhydride of 6-methoxy-6,7-dihydro-5H-1,4-dithiepine-2,3-dicarboxylic acid (10.0 g) in acetonitrile (150 cc), under reflux for 4½ hours.

Preparation of 6-hydroxy-3-methoxy-7-(7-methoxy-1,8-naphthyridin-2-yl)-8-oxo-3,4,7,8-tetrahydro-2$\underline{H}$,6$\underline{H}$-1,4-dithiepino[2,3-c]pyrrole (m.p. 192° C.; 10.7 g) by reacting potassium borohydride (1.32 g) with 6,8-dioxo-3-methoxy-7-(7-methoxy-1,8-naphthyridin-2-yl)-3,4,7,8-tetrahydro-2$\underline{H}$,6$\underline{H}$-1,4-dithiepino[2,3-c]pyrrole (12.7 g) in a mixture of tetrahydrofuran (100 cc) and methanol (30 cc) at between −10° C. and 0° C.

EXAMPLE 7

Triethylamine (24.5 cc) is added, at about 15° C., to a suspension of 6-hydroxy-3-methoxy-7-(7-methyl-1,8-naphthyridin-2-yl)-8-oxo-3,4,7,8-tetrahydro-2$\underline{H}$,6$\underline{H}$-1,4-dithiepino[2,3-c]pyrrole (7.3 g) and 1-chlorocarbonyl-4-methylpiperazine hydrochloride (11.7 g) in anhydrous methylene chloride (300 cc), and anhydrous pyridine (130 cc) is then added to the resulting mixture. The mixture is heated at 45° C. for 3 hours. 1-Chlorocarbonyl-4-methylpiperazine hydrochloride (6.0 g) is then added and the mixture is heated for a further ½ hour at 45° C. After cooling, the mixture is diluted by adding methylene chloride (300 cc). The organic phase is washed three times with distilled water (total 600 cc), dried over sodium sulphate and evaporated. The resulting residue (25.0 g) is dissolved in boiling acetonitrile (70 cc). After cooling the solution for 48 hours at 2° C., the resulting crystals are filtered off, washed twice with ice-cooled acetonitrile (total 20 cc) and dried under reduced pressure (20 mm Hg) at 20° C. The resulting product (5.25 g; m.p. 220° C.) is dissolved in methylene chloride (100 cc) and the solution is filtered through silica (0.2–0.5 mm; 200 g) contained in a column of diameter 2.1 cm. Elution is carried out with methylene chloride (400 cc); the eluate is discarded. Elution is continued with a mixture of methylene chloride (784 cc) and methanol (16 cc); this eluate is evaporated under reduced pressure (20 mm Hg) at a temperature below 60° C. The residue is dried under reduced pressure (0.2 mm Hg) at 50° C. 3-Methoxy-7-(7-methyl-1,8-naphthyridin-2-yl)-6-(4-methylpiperazin-1-yl)carbonyloxy-8-oxo-3,4,7,8-tetrahydro-2$\underline{H}$,6$\underline{H}$-1,4-dithiepino[2,3-c]pyrrole (4.2 g), melting at 225° C., is obtained.

6-Hydroxy-3-methoxy-7-(7-methyl-1,8-naphthyridin-2-yl)-8-oxo-3,4,7,8-tetrahydro-2$\underline{H}$,6$\underline{H}$-1,4-dithiepino[2,3-c]pyrrole used as starting material can be prepared in the following manner:

Preparation of 6,8-dioxo-3-methoxy-7-(7-methyl-1,8-naphthyridin-2-yl)-3,4,7,8-tetrahydro-2$\underline{H}$,6$\underline{H}$-1,4-dithiepino[2,3-c]pyrrole (m.p. 245° C.; 7.7 g) by reacting 2-amino-7-methyl-1,8-naphthyridine (5.9 g) and 3-(3-diethylaminopropyl)-1-isopropylcarbodiimide (8.1 g) with the anhydride of 6-methoxy-6,7-dihydro-5H-1,4-dithiepine-2,3-dicarboxylic acid (8.6 g) in acetonitrile (130 cc) under reflux for 6 hours.

Preparation of 6-hydroxy-3-methoxy-7-(7-methyl-1,8-naphthyridin-2-yl)-8-oxo-3,4,7,8-tetrahydro-2$\underline{H}$,6$\underline{H}$-1,4-dithiepino[2,3-c]pyrrole (m.p. 170° C.; 7.3 g) by reacting potassium borohydride (1.13 g) with 6,8-dioxo-3-methoxy-7-(7-methyl-1,8-naphthyridin-2-yl)-3,4,7,8-tetrahydro-2$\underline{H}$,6$\underline{H}$-1,4-dithiepino[2,3-c]pyrrole (10.4 g) in a mixture of tetrahydrofuran (80 cc) and methanol (24 cc) at between −10° C. and 0° C.

EXAMPLE 8

A solution of 1-propionylpiperazine (6.8 g) in anhydrous acetonitrile (50 cc) is added, at 20° C., to a suspension of 7-(5-chloropyrid-2-yl)-3-methoxy-8-oxo-6-phenoxycarbonyloxy-3,4,7,8-tetrahydro-2$\underline{H}$,6$\underline{H}$-1,4-dithiepino[2,3-c]pyrrole (11.15 g) in anhydrous acetonitrile (80 cc). The reaction mixture is heated under reflux for 6 hours. The acetonitrile is evaporated off under reduced pressure (20 mm Hg; 2.67 kPa). The residue is treated with water (100 cc) and extraction is carried out three times with methylene chloride (total 210 cc); the organic extracts are washed twice with distilled water (total 200 cc), dried over anhydrous sodium sulphate and evaporated to dryness. The resulting residue (14.7 g; oily) is dissolved in a mixture of chloroform and methanol (97:3 by volume; 50 cc). The solution is chromatographed on silica (0.04–0.063 mm; 400 g) contained in a column of diameter 6 cm, under a pressure of 140 kPa. Elution is carried out with the solvent mixture mentioned above under a pressure of 140 kPa. 1800 cc of eluate are collected and discarded, and then 600 cc of eluate are collected and evaporated to dryness under reduced pressure (20 mm Hg; 2.67 kPa). The resulting partially crystalline residue (11.0 g) is dissolved in a boiling mixture of acetonitrile (10 cc) and diisopropyl ether (50 cc). After cooling the solution for 2 hours at 2° C., the resulting crystals are filtered off, washed twice with diisopropyl ether (total 20 cc) and dried under reduced pressure (20 mm Hg; 2.67 kPa) at 20° C. The resulting product (4.1 g; m.p. 160° C.) is dissolved in boiling acetonitrile (60 cc). After cooling the solution for 2 hours at 2° C., the resulting crystals are filtered off, washed twice with diisopropyl ether (total 80 cc) and dried under reduced pressure (0.2 mm Hg; 0.026 kPa) at 50° C. 7-(5-Chloropyrid-2-yl)-3-methoxy-8-oxo-6-(4-propionylpiperazin-1-yl)carbonyloxy-3,4,7,8-tetrahydro-2H,6H-1,4-dithiepino[2,3-c]pyrrole (1.2 g), melting at 226° C., is obtained.

7-(5-Chloropyrid-2-yl)-3-methoxy-8-oxo-6-phenoxycarbonyloxy-3,4,7,8-tetrahydro-2H,6H-1,4-dithiepino[2,3-c]pyrrole used as starting material can be prepared in the following manner:

By reacting phenyl chloroformate (16.7 g) with 7-(5-chloropyrid-2-yl)-6-hydroxy-3-methoxy-8-oxo-3,4,7,8-tetrahydro-2H,6H-1,4-dithiepino[2,3-c]-pyrrole (prepared as described in Example 1; 12.3 g) in anhydrous pyridine (100 cc) at between −10° C. and +20° C., 7-(5-chloropyrid-2-yl)-3-methoxy-8-oxo-6-phenoxycarbonyloxy-3,4,7,8-tetrahydro-2H,6H-1,4-dithiepino[2,3-c]pyrrole (m.p. 167° C.; 10.1 g) is obtained.

1-Chlorocarbonyl-4-propionylpiperazine can be prepared as described in Example 5.

EXAMPLE 9

Isobutyric acid (2.20 cc) is added, in the course of 5 minutes, at 20° C. to a suspension of 7-(7-chloro-1,8-naphthyridin-2-yl)-3-methoxy-8-oxo-6-(piperazin-1-yl)carbonyloxy-3,4,7,8-tetrahydro-2H,6H-1,4-dithiepino[2,3-c]pyrrole (8.0 g) and dicyclohexylcarbodiimide (4.85 g) in anhydrous methylene chloride (160 cc). The reaction mixture is stirred for 1 hour at 20° C. The dicyclohexylurea formed is filtered off and washed twice with methylene chloride (total 20 cc). The filtrate is evaporated to dryness under reduced pressure (20 mm Hg; 2.67 kPa). The resulting crystals are treated with boiling ethanol (80 cc); the mixture is filtered hot and the insoluble crystals are washed with boiling ethanol (10 cc) and dried in air. The resulting product (7.6 g; m.p. 205° C.) is dissolved in boiling acetonitrile (80 cc) and the boiling solution is filtered. After cooling the filtrate for 4 hours at 2° C., the crystals which have formed are filtered off, washed twice with ice-cooled acetonitrile (total 15 cc) and dried under reduced pressure (0.2 mm Hg; 0.026 kPa) at 60° C. 7-(7-Chloro-1,8-naphthyridin-2-yl)-6-(4-isobutyrylpiperazin-1-yl)carbonyloxy-3-methoxy-8-oxo-3,4,7,8-tetrahydro-2H,6H-1,4-dithiepino[2,3-c]pyrrole (4.6 g), melting at 232° C., is thus obtained.

7-(7-Chloro-1,8-naphthyridin-2-yl)-3-methoxy-8-oxo-6-(piperazin-1-yl)carbonyloxy-3,4,7,8-tetrahydro-2H,6H-1,4-dithiepino[2,3-c]pyrrole used as starting material can be prepared in the following manner:

Preparation of 6-(4-t-butoxycarbonylpiperazin-1-yl)carbonyloxy-7-(7-chloro-1,8-naphthyrin-2-yl)-3-methoxy-8-oxo-3,4,7,8-tetrahydro-2H,6H-1,4-dithiepino[2,3-c]pyrrole (m.p. 210° C.; 32.0 g) by reacting t-butyl (4-chlorocarbonylpiperazin-1-yl)-carboxylate (27.4 g) with 7-(7-chloro-1,8-naphthyridin-2-yl)-6-hydroxy-3-methoxy-8-oxo-3,4,7,8-tetrahydro-2H,6H-1,4-dithiepino[2,3-c]pyrrole (prepared as described in Example 3; 27.2 g) in methylene chloride (280 cc), in the presence of anhydrous pyridine (140 cc) and triethylamine (9.7 cc), at about 50° C. for 8 hours.

Preparation of 7-(7-chloro-1,8-naphthyridin-2-yl)-3-methoxy-8-oxo-6-(piperazin-1-yl)carbonyloxy-3,4,7,8-tetrahydro-2H,6H-1,4-dithiepino[2,3-c]pyrrole (m.p. about 320° C.; 13.0 g) by reacting trifluoroacetic acid (190 cc) with 6-(4-t-butoxycarbonylpiperazin-1-yl)carbonyloxy-7-(7-chloro-1,8-naphthyridin-2-yl)-3-methoxy-8-oxo-3,4,7,8-tetrahydro-2H,6H-1,4-dithiepino[2,3-c]pyrrole (32.0 g) at −5° C., for 1 hour.

t-Butyl (4-chlorocarbonylpiperazin-1-yl)carboxylate can be prepared in the following manner:

Preparation of t-butyl piperazin-1-ylcarboxylate (m.p. 60° C.; 91.0 g) by reacting t-butoxycarbonylazide (259.0 g) with piperazine monohydrochloride (310.0 g) in a mixture of water and dioxan (1:2 by volume) at 45° C.

Preparation of t-butyl (4-chlorocarbonylpiperazin-1-yl)carboxylate (m.p. 99° C.; 24.8 g) by reacting phosgene (11.0 g) with t-butyl piperazin-1-ylcarboxylate (40.8 g) in toluene at −5° C.

EXAMPLE 10

By following the procedure of Example 9 but starting with 7-(7-chloro-1,8-naphthyridin-2-yl)-3-methoxy-8-oxo-6-(piperazin-1-yl)carbonyloxy-3,4,7,8-tetrahydro-2H,6H-1,4-dithiepino[2,3-c]pyrrole (1.0 g), dicyclohexylcarbodiimide (0.61 g) and propionic acid (0.22 cc) in methylene chloride (20 cc), 7-(7-chloro-1,8-naphthyridin-2-yl)-3-methoxy-8-oxo-6-(4-propionylpiperazin-1-yl)carbonyloxy-3,4,7,8-tetrahydro-2H, 6H-1,4-dithiepino[2,3-c]pyrrole (0.57 g), melting at 216° C., is obtained.

The present invention includes within its scope pharmaceutical compositions which comprise, as active ingredient, at least one of the compounds of general formula I, or—when appropriate—a non-toxic acid addition salt thereof, in association with a pharmaceutically acceptable carrier, adjuvant or coating. The invention includes especially such preparations made up for oral, parenteral, rectal or percutaneous administration.

Solid compositions for oral administration include tablets, pills, powders and granules. In such solid compositions the active compounds is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material (preferably gelatin) containing the active substance with or without the addition of diluents or excipients, e.g. in the form of a powder.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

Compositions for percutaneous administration are creams, ointments, lotions and liniments, in which the active substance is associated with liquid or pasty excipients, preferably in association with a vehicle which assists percutaneous migration.

The pharmaceutical compositions according to the invention are particularly useful in human therapy by virtue of their tranquillising, anti-convulsive, decontracturant and hypnogenic action.

In human therapy, the doses of active ingredient depend on the desired effect and the duration of the treatment; for an adult, they are generally between 0.5 and 25 mg of active substance per day, administered orally.

In general, the physician will determine the posology considered appropriate, taking into account the age, weight and all the other factors intrinsic to the patient to be treated.

The following Example illustrates pharmaceutical compositions according to the invention.

EXAMPLE 11

Tablets containing 5 mg doses of active product and having the following composition are prepared in accordance with the usual technique:

| | |
|---|---|
| form A of 7-(7-chloro-1,8-napthyridin-2-yl)-3-methoxy-6-(4-methylpiperazin-1-yl)carbonyloxy-8-oxo-3,4,7,8-tetrahydro-2H,6H-1,4-dithiepino[2,3-c]pyrrole | 0.005 g |
| starch | 0.100 g |
| precipitated silica | 0.018 g |
| magnesium stearate | 0.002 g |

We claim:

1. A 1,4-dithiepino[2,3-c]pyrrole compound of the formula:

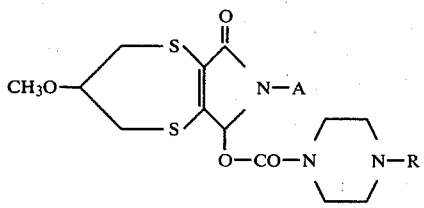

wherein A represents pyrid-2-yl, quinol-2-yl or 1,8-naphthyridin-2-yl, or pyrid-2-yl, quinol-2-yl or 1,8-naphthyridin-2-yl substituted by one halogen, alkyl of 1 through 4 carbon atoms or alkoxy of 1 through 4 carbon atoms, and R represents hydrogen, alkyl of 1 through 4 carbon atoms or alkanoyl of 1 through 4 carbon atoms, and when R is hydrogen or alkyl non-toxic pharmaceutically acceptable acid addition salts thereof.

2. A 1,4-dithiepino[2,3-c]pyrrole compound according to claim 1 wherein A represents pyrid-2-yl or 1,8-naphthyridin-2-yl, or pyrid-2-yl or 1,8-naphthyridin-2-yl substituted by one halogen or alkoxy of 1 through 4 carbon atoms, and R represents alkyl of 1 through 4 carbon atoms.

3. A 1,4-dithiepino[2,3-c]pyrrole compound according to claim 1 or 2 in which the halogen is chlorine, the alkyl is methyl, the alkoxy is methoxy, and the alkanoyl is propionyl or isobutyryl.

4. The 1,4-dithiepino[2,3-c]pyrrole compound according to claim 1 which is 7-(5-chloropyrid-2-yl)-3-methoxy-6-(4-methylpiperazin-1-yl)carbonyloxy-8-oxo-3,4,7,8-tetrahydro-2H,6H-1,4-dithiepino[2,3-c]pyrrole and its non-toxic pharmaceutically acceptable acid addition salts.

5. The 1,4-dithiepino[2,3-c]pyrrole compound according to claim 1 which is 7-(7-chloroquinol-2-yl)-3-methoxy-6-(4-methylpiperazin-1-yl)carbonyloxy-8-oxo-3,4,7,8-tetrahydro-2H,6H-1,4-dithiepino[2,3-c]pyrrole and its non-toxic pharmaceutically acceptable acid addition salts.

6. The 1,4-dithiepino[2,3-c]pyrrole compound according to claim 1 which is 7-(7-chloro-1,8-naphthyridin-2-yl)-3-methoxy-6-(4-methylpiperazin-1-yl)carbonyloxy-8-oxo-3,4,7,8-tetrahydro-2H,6H-1,4-dithiepino[2,3-c]pyrrole and its non-toxic pharmaceutically acceptable acid addition salts.

7. The 1,4-dithiepino[2,3-c]pyrrole compound according to claim 1 which is 7-(7-chloro-1,8-naphthyridin-2-yl)-3-methoxy-8-oxo-6-(4-propionylpiperazin-1-yl)carbonyloxy-3,4,7,8-tetrahydro-2H,6H-1,4-dithiepino[2,3-c]pyrrole.

8. The 1,4-dithiepino[2,3-c]pyrrole compound according to claim 1 which is 3-methoxy-7-(7-methoxy-1,8-naphthyridin-2-yl)-6-(4-methylpiperazin-1-yl)carbonyloxy-8-oxo-3,4,7,8-tetrahydro-2H,6H-1,4-dithiepino[2,3-c]pyrrole and its non-toxic pharmaceutically acceptable acid addition salts.

9. The 1,4-dithiepino[2,3-c]pyrrole compound according to claim 1 which is 3-methoxy-7-(7-methyl-1,8-naphthyridin-2-yl)-6-(4-methylpiperazin-1-yl)carbonyloxy-8-oxo-3,4,7,8-tetrahydro-2H,6H-1,4-dithiepino[2,3-c]pyrrole and its non-toxic pharmaceutically acceptable acid addition salts.

10. The 1,4-dithiepino[2,3-c]pyrrole compound according to claim 1 which is 7-(5-chloropyrid-2-yl)-3-methoxy-8-oxo-6-(4-propionylpiperazin-1-yl)carbonyloxy-3,4,7,8-tetrahydro-2H,6H-1,4-dithiepino[2,3-c]pyrrole.

11. The 1,4-dithiepino[2,3-c]pyrrole compound according to claim 1 which is 7-(7-chloro-1,8-naphthyridin-2-yl)-6-(4-isobutyrylpiperazin-1-yl)carbonyloxy-3-methoxy-8-oxo-3,4,7,8-tetrahydro-2H,6H-1,4-dithiepino[2,3-c]pyrrole.

12. The 1,4-dithiepino[2,3-c]pyrrole compound according to claim 1 which is 7-(7-chloro-1,8-naphthyridin-2-yl)-3-methoxy-8-oxo-6-(4-propionylpiperazin-1-yl)carbonyloxy-3,4,7,8-tetrahydro-2H,6H-1,4-dithiepino[2,3-c]pyrrole.

13. A pharmaceutical composition useful as a tranquilliser, anti-convulsant, decontracturant or a hypnogenic agent consisting essentially of, as an active ingredient an effective amount of a 1,4-dithiepino[2,3-c]pyrrole compound as claimed in claim 1, or—when R in the formula represents hydrogen or alkyl—a non-toxic pharmaceutically acceptable acid addition salt thereof, in association with a significant amount of a pharmaceutical carrier.

* * * * *